United States Patent
Ziegler et al.

(10) Patent No.: US 11,094,409 B2
(45) Date of Patent: Aug. 17, 2021

(54) APPLICATION UNLOCK USING A CONNECTED PHYSICAL DEVICE AND TRANSFER OF DATA THEREBETWEEN

(71) Applicants: Dominik Ziegler, Basel (CH); Manfred Mueller, Dagmerselle (CH)

(72) Inventors: Dominik Ziegler, Basel (CH); Manfred Mueller, Dagmerselle (CH)

(73) Assignee: Novartis AG, Basel (CH)

( * ) Notice: Subject to any disclaimer, the term of this patent is extended or adjusted under 35 U.S.C. 154(b) by 552 days.

(21) Appl. No.: 15/544,349

(22) PCT Filed: Jan. 19, 2016

(86) PCT No.: PCT/IB2016/050242
§ 371 (c)(1),
(2) Date: Jul. 18, 2017

(87) PCT Pub. No.: WO2016/116853
PCT Pub. Date: Jul. 28, 2016

(65) Prior Publication Data
US 2018/0011988 A1 Jan. 11, 2018

Related U.S. Application Data

(60) Provisional application No. 62/105,306, filed on Jan. 20, 2015.

(51) Int. Cl.
*G16H 40/60* (2018.01)
*G06F 21/30* (2013.01)
(Continued)

(52) U.S. Cl.
CPC .......... *G16H 20/13* (2018.01); *G06F 21/305* (2013.01); *G06F 21/35* (2013.01); *G16H 40/63* (2018.01); *G16H 40/67* (2018.01)

(58) Field of Classification Search
None
See application file for complete search history.

(56) References Cited

U.S. PATENT DOCUMENTS 8,479,730 B2   7/2013  Ziegler
8,932,250 B2 * 1/2015  Montgomery ......... G16H 40/67
                                                              604/67

(Continued)

FOREIGN PATENT DOCUMENTS

CN      103927019 A    7/2014
EP       1850226 A1    10/2007

(Continued)

OTHER PUBLICATIONS

Uher, Jason et al., I2MeDS: Intelligent Integrated Medical Data System, 2008 Int'l Conference on Biomedical Engineering Informatics, 2008, pp. 631-637, https://ieeexplore.ieee.org/stamp/stamp.jsp?tp=&arnumber=4548746 (last visited Apr. 13, 2021) (Year: 2008).*

*Primary Examiner* — Elaine Gort
*Assistant Examiner* — Nicholas Akogyeram, II
(74) *Attorney, Agent, or Firm* — Guy Tucker; Michael Mazza

(57) ABSTRACT

According to one embodiment, a system includes a medical device configured to provide a function to a user, communicate via a wireless communication channel with one or more other devices, and send a signal to shift a medical device application from a locked state to an unlocked state. The system also includes a computing device having wireless communication channels and a processor and logic integrated with and/or executable by the processor. The logic is configured to cause the computing device to communicate with the medical device, execute the medical device application, and shift from the locked state to the unlocked state in response to receiving the signal from the medical device.

(Continued)

Core functionality of the medical device application is disabled when the medical device application is in the locked state, and some functionality applicable to the medical device is enabled when the medical device application is in the unlocked state.

20 Claims, 8 Drawing Sheets

(51) Int. Cl.
  *G06F 21/35* (2013.01)
  *G16H 20/10* (2018.01)
  *G16H 20/13* (2018.01)
  *G16H 40/63* (2018.01)
  *G16H 40/67* (2018.01)

(56) References Cited

U.S. PATENT DOCUMENTS

| | | |
|---|---|---|
| 2003/0086338 A1 | 5/2003 | Sastry et al. |
| 2005/0274378 A1* | 12/2005 | Bonney ............ A61M 15/0045 128/200.23 |
| 2007/0146130 A1 | 6/2007 | Hannemann et al. |
| 2008/0001735 A1 | 1/2008 | Tran et al. |
| 2008/0132973 A1 | 6/2008 | Lord et al. |
| 2008/0312584 A1* | 12/2008 | Montgomery .... A61M 5/14244 604/67 |
| 2011/0006876 A1* | 1/2011 | Moberg ............ G06F 19/3418 340/3.2 |
| 2011/0012742 A1 | 1/2011 | Johnson et al. |
| 2012/0083716 A1 | 4/2012 | Yuen et al. |
| 2012/0322371 A1 | 12/2012 | Lee et al. |
| 2013/0332197 A1 | 12/2013 | Hinkel et al. |
| 2014/0000603 A1 | 1/2014 | Hosemann |

FOREIGN PATENT DOCUMENTS

| | | | |
|---|---|---|---|
| JP | 2011-092418 | 5/2011 | |
| WO | 2001/45014 A1 | 6/2001 | |
| WO | WO-2004011071 A1 * | 2/2004 | ........ A61M 15/0093 |
| WO | 2005/011249 A1 | 2/2005 | |
| WO | 2005/045608 A2 | 5/2005 | |
| WO | 2005/122879 A1 | 12/2005 | |
| WO | 2006/108304 A1 | 10/2006 | |
| WO | 2007/084668 A2 | 7/2007 | |
| WO | 2008/069829 A1 | 6/2008 | |
| WO | 2010/035202 A1 | 4/2010 | |
| WO | 2010/044911 A1 | 4/2010 | |
| WO | 2010/078558 A1 | 7/2010 | |
| WO | 2010/117854 A1 | 10/2010 | |
| WO | WO 2011/005633 | 1/2011 | |
| WO | 2012/044519 A1 | 4/2012 | |
| WO | 2013/078064 A1 | 5/2013 | |
| WO | 2013/112978 A1 | 8/2013 | |
| WO | 2013/113756 A1 | 8/2013 | |
| WO | 2014/015293 A1 | 1/2014 | |
| WO | 2014/088236 A1 | 6/2014 | |
| WO | 2014/116505 A1 | 7/2014 | |
| WO | 2014/140121 A1 | 9/2014 | |
| WO | 2014/173867 A1 | 10/2014 | |
| WO | 2014/204511 A2 | 12/2014 | |

\* cited by examiner

APPLICATION UNLOCK USING A CONNECTED PHYSICAL DEVICE AND TRANSFER OF DATA THEREBETWEEN

FIELD OF THE INVENTION

The present invention relates to software applications, and more particularly, this invention relates to unlocking a software application using a connected physical device and transferring data therebetween.

BACKGROUND

Many different types of devices may make use of software applications. The devices may have a variety of different functionalities, including, for example, health and fitness such as activity tracking, monitoring, sensing, as well as serving medical needs or services. In particular, medical devices are available for use by patients and/or healthy subjects, for a variety of different functions, that may make use of software applications. These medical devices may include, for example, active and/or passive sensing devices, diagnostic devices for condition and/or disease state, drug administration devices, corrective and conditioning devices, and therapy administration devices, among others. The devices may be specific to a particular function, intended use, patient needs, ailment being treated or diagnosed, methods of interaction with the body, or may perform a combination of one or more of the foregoing. Some intended uses of medical devices comprise monitoring one or more physiological parameters, providing medicament to a patient (which may be provided orally, through injection, by inhalation, etc.) administering electrical stimulation to certain parts of a patient's body, stimulating certain parts of a patient's body via changes in physical state (such as temperature, hydration, pressure, etc.), and/or combinations thereof. Some exemplary medical devices include pacemakers, heart monitors, metabolite and/or substance monitors (e.g., glucose monitors), inhalers and nebulizers, substance (drug or pharmaceutical) delivery devices such as drug injection syringes (e.g., pens), auto-injectors, and imaging and/or scanning devices. Some medical devices require a prescription in order to obtain them, and some are available "over the counter" without a prescription.

For medical devices which require a prescription, once the medical device is provided to the patient for whom the prescription was supplied by a heath care provider, it is generally the patient who is responsible for ensuring compliance with the prescription and/or proper usage of the device. As such there are limited techniques available to ensure that the prescription and/or medical device is not misused, either by the patient or by someone who is not in possession of a prescription to use such a medical device.

Furthermore, most medical devices do not include a mechanism that ensures that proper usage of the medical device is always followed, such as accurately administering medicament only to patients having a prescription, administering the correct medicament and dosage to the patient for the designated disease or condition, providing medicament only as instructed by the prescribing doctor, limiting the amount of medicament available over a certain time period, etc. Also, most medical devices do not have a mechanism for tracking statistics associated with the usage of the medical device, such as frequency of use, amount of medicament dispersed, time of usage, and dose compliance. Instead, most common medical devices rely on a patient's ability to track and administer the medicament with only a doctor's instructions on how to do so.

SUMMARY

According to one embodiment, a system includes a medical device configured to provide a function to a user of the medical device, communicate via a wireless communication channel with one or more other devices, and send a signal to shift a medical device application from a first state to a second state, for example a locked state to an unlocked state. The system also includes a computing device having one or more wireless communication channels and a processor and logic integrated with and/or executable by the processor, the logic being configured to cause the computing device to communicate with the medical device, execute the medical device application, and shift from the first or locked state to the second or unlocked state in response to receiving the signal from the medical device. Certain functionalities of the medical device application may be disabled when the medical device application is in the locked state, and at least some functionality applicable to the medical device is enabled when the medical device application is in the unlocked state. For example, a core functionality of the medical device application may be disabled when in the locked state, and some or all functionality of the medical device application may be enabled in the unlocked state.

In another embodiment, a method includes providing, using a medical device, a function to a user of the medical device, communicating via a wireless communication channel with one or more other devices, and sending a signal to shift a medical device application executing on a computing device from a first, e.g., locked state to a second, e.g. unlocked state.

Other aspects and embodiments of the present invention will become apparent from the following detailed description, which, when taken in conjunction with the drawings, illustrate by way of example the principles of the invention.

DETAILED DESCRIPTION

Figure 1:
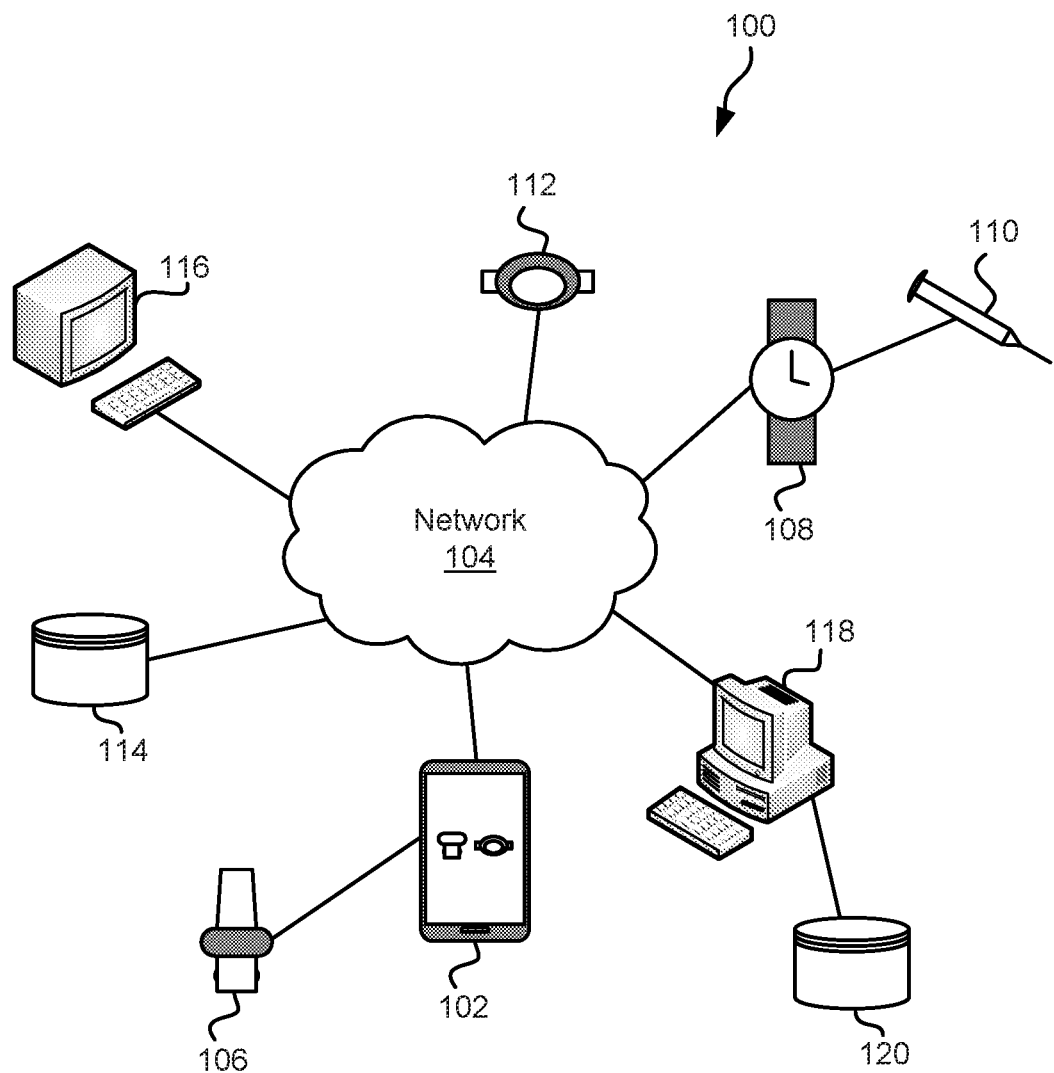
FIG. 1 shows a network architecture, in accordance with embodiments of the present invention.

The following description is made for the purpose of illustrating the general principles of the present invention and is not meant to limit the inventive concepts claimed herein. Further, particular features, aspects or elements described herein in connection with one embodiment can be used in combination with other described features, aspects or elements in each of the various possible combinations and permutations among the disclosed embodiments.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an," and "the" include plural unless otherwise specified.

According to one general embodiment, a system includes a medical device configured to provide a function to a user of the medical device, communicate via a wireless communication channel with one or more other devices, and send a signal to shift a medical device application from a first or locked state to a second or unlocked state. The system also includes a computing device having one or more wireless communication channels and a processor and logic integrated with and/or executable by the processor, the logic being configured to cause the computing device to communicate with the medical device, execute the medical device application, and shift from the first state to the second state in response to receiving the signal from the medical device. In many embodiments, the first state is a locked state or condition, and the second state is an unlocked state or condition. In embodiments of the invention, a core functionality of the medical device application is disabled when the medical device application is in the locked state, and at least some functionality applicable to the medical device is enabled when the medical device application is in the unlocked state.

In another general embodiment, a method includes providing, using a medical device, a function to a user of the medical device, communicating via a wireless communication channel with one or more other devices, and sending a signal to shift a medical device application executing on a computing device from a first or locked state to second or unlocked state.

The description herein is presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention Thus, the present invention is not intended to be limited to the embodiments shown, but is to be accorded the widest scope consistent with the principles and features disclosed herein.

In particular, various embodiments of the invention discussed herein are implemented using the Internet as a means of communicating with or between a physical device and a computer or a plurality of computer systems. One skilled in the art will recognize that the present invention is not limited to the use of the Internet as a communication medium and that alternative methods of the invention may accommodate the use of a private intranet, a Local Area Network (LAN), a Wide Area Network (WAN) or other means of communication. In addition, various combinations of wired, wireless (e.g., radio frequency) and optical communication (e.g., visible or infrared) links may be utilized. In some embodiments, communications may be achieved via human audible or inaudible sound. Furthermore, communication may be made between devices using quick response (QR) codes, bar codes, radio frequency identification (RFID) tags and devices, or video and image capture technology.

The program environment in which one embodiment of the invention may be executed illustratively incorporates one or more general-purpose computers or special-purpose devices such hand-held computers. Details of such devices (e.g., processor, memory, data storage, input, and output devices) are well known and are omitted for the sake of clarity.

It should also be understood that the techniques of the present invention might be implemented using a variety of technologies. For example, the methods described herein may be implemented in software running on a computer system, and/or implemented in hardware utilizing one or more processors and logic (hardware and/or software) for performing operations of the method, application specific integrated circuits (ASICs), programmable logic devices such as field programmable gate arrays (FPGAs), and/or various combinations thereof. In one illustrative approach, methods described herein may be implemented by a series of computer executable instructions residing on a storage medium, such as a physical (e.g., non-transitory) computer readable medium. In addition, although specific embodiments of the invention may employ object-oriented software programming concepts, the invention is not so limited and is easily configurable to employ other forms of directing the operation of a computer.

The invention may also be provided in the form of a computer program product comprising a computer readable storage or signal medium having computer code thereon, which may be executed by a computing device (e.g., one or more processors), a system, and/or some other suitable device. A computer readable storage medium may include any medium capable of storing computer code thereon for use by a computing device or system, including optical media such as read only and rewriteable CD and DVD, magnetic memory and/or media (e.g., hard disk drive, tape, etc.), semiconductor memory (e.g., volatile fast access memory, nonvolatile memory, portable memory cards, etc.), or firmware encoded in a microchip.

A computer readable signal medium is one that does not normally fit within the aforementioned computer readable storage medium class. For example, illustrative computer readable signal media communicate or otherwise transfer transitory signals within a system or between systems, e.g., via one or more physical and/or virtual networks. For example, a computer readable signal medium may include any communication signal that is sent and/or received from one or more devices in a network, by one or more of a variety of free space or physical media data transfer standards and/or protocols. these may include for example Ethernet packets sent across an Ethernet connection, wireless data packets sent across a WIFI network, control signals sent between interconnected devices via copper wiring, optical communications sent over free space or physical links, etc.

FIG. 1 illustrates a network architecture 100, in accordance with one embodiment. As an option, the present network architecture 100 may be implemented in conjunction with features from any other embodiment listed herein, such as those described with reference to the other figures. Of course, however, such network architecture 100 and others presented herein may be used in various applications and/or in permutations which may or may not be specifically described in the illustrative embodiments listed herein.

Further, the network architecture 100 presented herein may be used in any desired environment.

As shown in FIG. 1, a computing device 102 (which is illustrated as a smart phone but is not so limited) is shown in communication with a network 104 and a medical device 106 (which is illustrated as a smart inhaler, but is not so limited).

The network 104 may take any network form including, but not limited to a local area network (LAN), a wide area network (WAN) such as the Internet, a wireless local area network (WLAN) such as WIFI, public switched telephone network (PSTN), internal telephone network, etc. In more embodiments, the network 104 may include a plurality of networks which are interconnected. The networks may be remote from one another, and may span many geographical areas, and possibly around the world. Further, one or more gateways may be coupled between any of the networks and the network 104, and/or may be coupled between the devices connecting to the network 104 locally. In use, the one or more gateways may serve as entrance points for data to be sent across the network 104 and any networks therein. As such, the one or more gateways may function as routers, which are capable of directing a given packet of data that arrives at the gateway, and a switch, which furnishes the actual path in and out of the gateway for a given packet.

The network architecture 100 also shows other exemplary computing devices connected to the network 104, including a smart watch 108 connected to a smart syringe 110, so that the smart watch 108 is configured to upload and/or download information relating to the functionality of the smart syringe 110 and use thereof from the network 104.

In another use case, a heart rate monitor 112 is shown connected directly to the network 104. In this embodiment, the heart rate monitor 112 is configured to communicate directly through the network 104 to one or more devices for uploading and/or downloading information relating to the functionality and usage of the heart rate monitor 112.

Some other devices connected to the network 104 and possibly accessible to any of the other devices connected to the network 104 include storage 114, a workstation 116, and a server 118. The storage 114 may include any type of memory known in the art for storing information therein, such as (with reference to FIGS. 1-2) random access memory (RAM) 214, read only memory (ROM) 216, magnetic tape media, hard disk media, optical disk media, non-volatile memory such as flash memory, etc. Furthermore, the storage 114 may be used by any of the other devices for storage of information and/or data therein, such as by the smart phone 102 for storing usage data about the inhaler 106. Also, the storage 114 may be used by any of the other devices connected to the network 104 for retrieval of information and/or data therefrom, such as by the smart watch 108 for retrieving information on a dosage and/or a dosage regimen the smart syringe 110 is configured to inject. For example this may relate to any or all of a dosage amount, range, a maximum, a minimum, and acceptable deviation from a nominal dose.

The workstation 116 may take the form of any type of computing device known in the art, such as a desktop computer, laptop computer, hand-held computer, printer, or any other type of user device or logic.

Further included is at least one server 118 coupled to the network 104, and which is possibly accessible from the other devices connected to the network 104. It should be noted that the server(s) 118 may include any type of computing device/groupware. Each server 118 may have connected thereto a plurality of user devices (not shown) and/or storage 120. Such user devices may include a desktop computer, laptop computer, hand-held computer, printer, or any other type of user device or logic. It should be noted that a user device may also be directly coupled to the network 104, in one embodiment.

According to some approaches, methods and systems described herein may be implemented with and/or on virtual systems and/or systems which emulate one or more other systems, such as a UNIX system which emulates a MAC OS environment, a UNIX system which virtually hosts a MICROSOFT WINDOWS environment, a MICROSOFT WINDOWS system which emulates a MAC OS environment, and others known in the art. This virtualization and/or emulation may be enhanced through the use of VMWARE software, in some embodiments.

In more approaches, one or more networks may represent a cluster of systems commonly referred to as a "cloud." In cloud computing, shared resources, such as processing power, connected storage, peripherals, software, data processing, and/or storage, servers, etc., are provided to any device or system in the cloud, preferably in an on-demand relationship, thereby allowing access and distribution of services across many computing systems. Cloud computing typically involves an Internet and/or other high speed data connection (e.g., 4G LTE, fiber optic, etc.) between the systems operating in the cloud, but other techniques of connecting the systems may also be used, such as WiFi, Bluetooth, etc.

In one embodiment, data may be stored to the cloud by one or more medical devices which are configured to communicate with a device in the cloud capable of storing such data. This cloud data storage may be utilized whenever the one or more medical devices are capable of communicating with the device in the cloud and have data to be stored therein. Alternatively or additionally, the one or more medical devices may have local data storage capability, and may utilize the cloud as backup storage and/or overflow storage for data stored locally to the one or more medical devices. In either of these embodiments, when the one or more medical devices communicate with a computing device, the computing device is also provided with access to the data stored to the cloud, either directly by accessing the device storing the data in the cloud, or by receiving the data from the one or more medical devices, which access the data stored to the cloud and send it to the computing device. One of skill in the art would be able to appreciate and understand many other uses of data storage on the cloud, and those uses may be implemented in the embodiments described herein without specifically reciting all such combinations.

Figure 2:
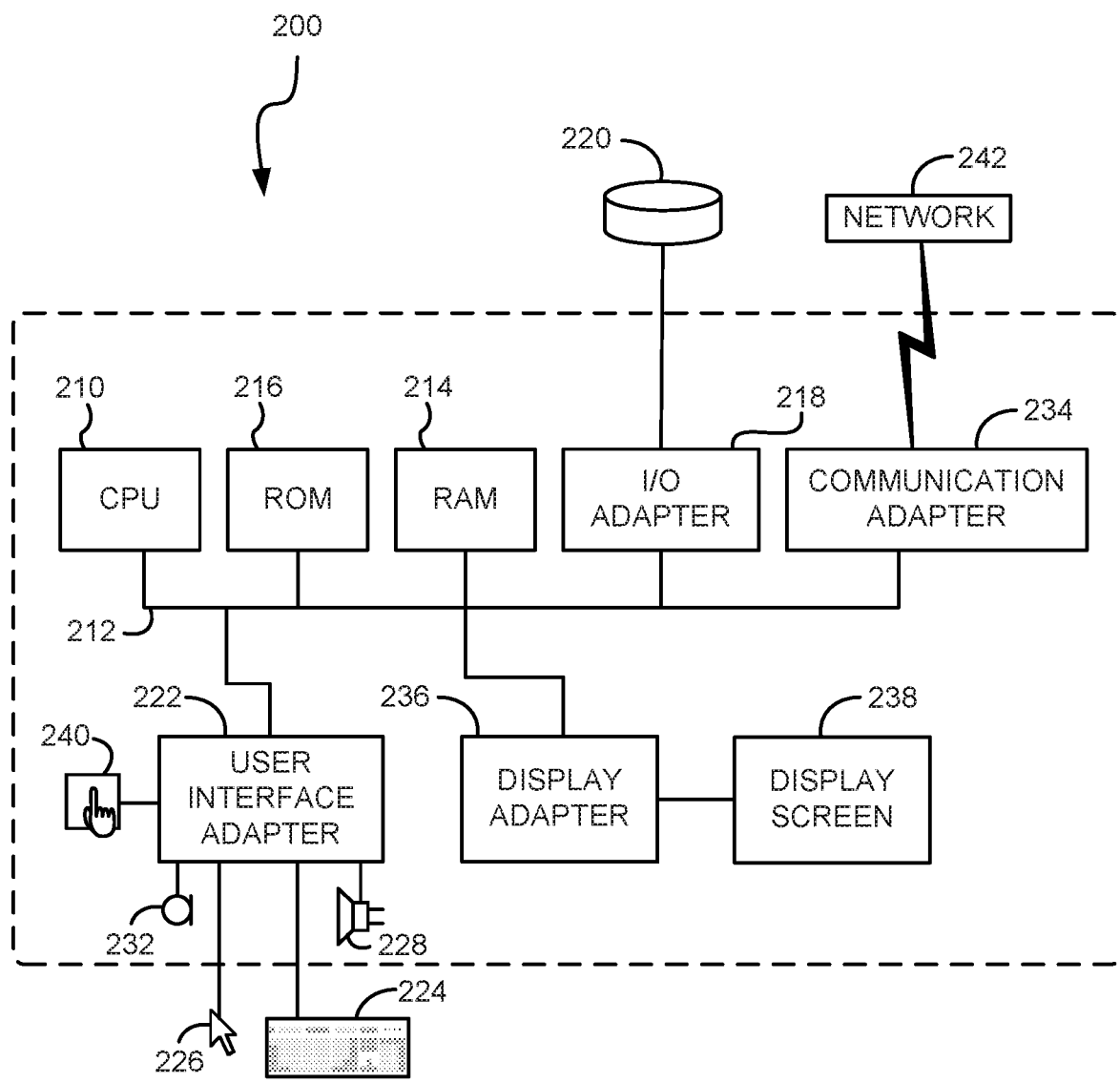
FIG. 2 shows a representative computing device, according to an embodiment of the present invention.

FIG. 2 shows an exemplary computing device 200, in accordance with one embodiment. The representative computing device 200 may include a central processing unit 210, such as a microprocessor, and a number of other units interconnected via a system bus 212.

The computing device 200 shown in FIG. 2 includes RAM 214, ROM 216, an I/O adapter 218 for connecting external devices such as memory 220 to the bus 212, a user interface adapter 222 for connecting various user interface devices to the bus 212, such as those internal to the computing device 200 (e.g., a touch screen interface 240, a speaker 228, a microphone 232) and devices external to the computing device 200 (e.g., a keyboard 224, a mouse 226, etc.), a communication adapter 234 for connecting the computing device 200 to a network 242 (e.g., a data processing network, communication network, etc.) and a display adapter 236 for connecting the bus 212 to a display screen 238 (which is shown internal to the computing device 200 but may be an external display).

The computing device 200 may have resident thereon an operating system, such as the MICROSOFT WINDOWS Operating System (OS), a MAC OS, a UNIX OS, ANDROID, APPLE iOS, or others known in the art. It will be appreciated that embodiments of the present invention may also be implemented on platforms and operating systems other than those mentioned. Embodiments of the present invention may be written using JAVA, XML, C, and/or C++ language, or other programming languages, along with an object oriented programming methodology. Object oriented programming (OOP), which has become increasingly used to develop complex applications, may be used.

Figure 3:
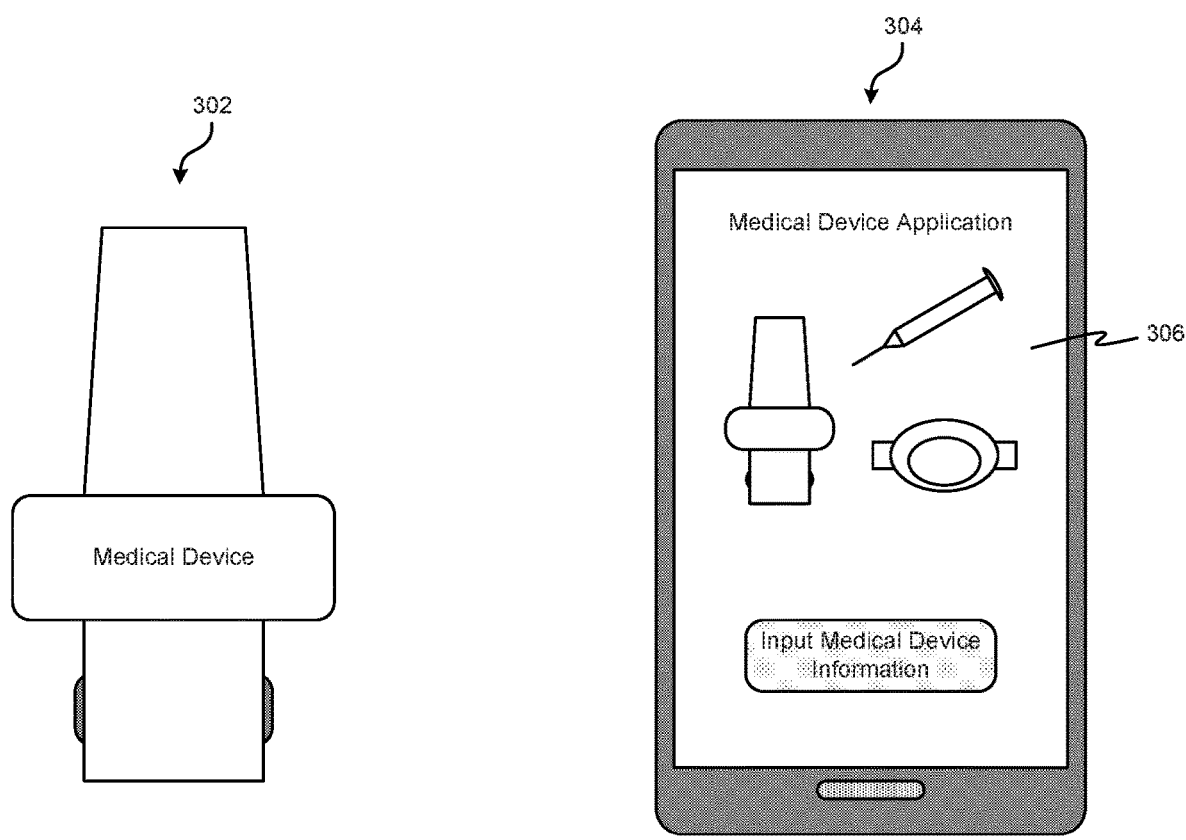
FIG. 3 shows a medical device and a computing device, according to an embodiment of the present invention.

Now referring to FIG. 3, a medical device 302 is shown along with a computing device 304, according to one embodiment. In this embodiment, the computing device 304 may comprise any computing device known in the art, such as a personal computer (PC), a mobile telephone (e.g., a smart phone (such as APPLE iPHONE, SAMSUNG GALAXY S3, S4, S5, etc.), cell phone, etc.), a tablet computer (such as an APPLE iPAD, MICROSOFT SURFACE, SAMSUNG GALAXY TAB, AMAZON KINDLE, etc.), a smart watch (e.g., MOTOROLA MOTO360, ASUS ZENWATCH, APPLE iWATCH, etc.), a laptop computer, an ultrabook computer, or a wearable device (e.g., head-up displays including GOGGLE GLASS and others, tracking and displaying devices like FITBIT). The computing device 302 is capable of communicating via one or more wireless communication technologies. Any wireless communication technology capable of receiving a signal and transmitting data to/from the medical device 302 may be used, as would be known to one of skill in the art upon reading the present description.

In embodiments of the present invention, the computing device 304 is a smart phone, as shown, capable of downloading program applications from a central application server. Any central application server may be used to download program applications, such as APPLE APP STORE, APPLE iTUNES, GOOGLE PLAY STORE, AMAZON APP STORE, etc. Any of these application servers may include a medical device application 306 that may be downloaded onto the computing device 304. Medical device applications may also be downloadable from servers under the control of the provider of the medical device, healthcare providers, pharmacies, hospitals, clinicians, or doctors.

In some embodiments, the medical device 302 may be any medical device known in the art capable of communicating with the computing device 304 via a wireless communication technology. Any wireless communication technology may be used for transmitting the signal from the medical device 302 to the medical device application 306, as would be known to one of skill in the art upon reading the present descriptions.

Some exemplary wireless communication technologies include, but are not limited to, Bluetooth, Bluetooth low energy (BLE), ZIGBEE, Z-WAVE, infrared (IR), WLAN such as WIFI, RF, near-field communication (NFC), and optical.

In another embodiment, a proprietary wireless communication protocol may be used to send information between the medical device 302 and the computing device 304, with the proprietary communication protocol being configured to effectively convey information specific to the medical device 302 and uses thereof.

In some examples, the medical device 302 may comprise a WIFI-enabled glucose meter, an RF-capable heart monitor, a smart syringe capable of altering dosages based on one or more criteria and can communicate via NFC, a Bluetooth-capable implantable insulin injector. Combinations and permutations of the foregoing devices and communications protocols are contemplated. In one embodiment, the medical device 302 is an inhaler configured to communicate wirelessly. In some embodiments, the wireless standard or protocol comprises BLE and/or Bluetooth.

In some further embodiments, the medical device 302 may comprise a processor capable of executing logic, a local memory for storing data, and logic which may be accessible to the processor and/or implemented within the processor. The logic may be configured to cause the medical device to follow instructions from the computing device, send information from the medical device 302 to the computing device 304, a networked storage device, other devices within a network, and/or a cloud, and receive information from the computing device 304, a networked storage device, other devices within a network, and/or a cloud.

The local memory of the medical device 302 may comprise any memory known to one of skill in the art, such as RAM, ROM, non-volatile memory (NVM) such as Flash memory, removable memory such as a microSD card.

In accordance with one embodiment, a user of the computing device 304 may install a medical device application 306 on the computing device 304. The medical device application 306 may be downloaded from an application server accessible to the computing device 304, the application server being of a type known in the art. In another embodiment, the medical device application 306 may be provided to the computing device 304, for example via a computer readable storage medium, such as a CD, MicroSD card, RAM, or ROM, and/or virtually provided via a link and/or pointer that is embedded in a communication received by the computing device 304, such as a hypertext link in an email, or HTML pointer in a text message. The computing device 304 may then access the medical device application 306 via the Internet, a WLAN such as a WIFI network, a WAN, a LAN, etc., to install the medical device application 306 on the computing device 304, as would be understood by one of skill in the art upon reading the present descriptions.

After the user has caused the medical device application 306 to become installed on the computing device 304 and started, executed, run, and/or opened the medical device application 306 on the computing device 304, the medical device application 306 will indicate that it is in a first state, which may be a locked state wherein the medical device application 306 will not provide functionality, or will not provide desired or complete functionality. Once the medical device application 306 has been shifted from the first or locked state to the second or unlocked state, the medical device application 306 will provide the functionality, or full or complete or desired functionality, as shown in FIG. 4, in accordance with one embodiment.

In an alternate embodiment, the medical device application 306 may be unlocked upon installation, and will allow the user to access all functionality thereof. However, a medical device 302 may not function unless it has been paired with and/or unlocked by the medical device application 306.

Figure 4:
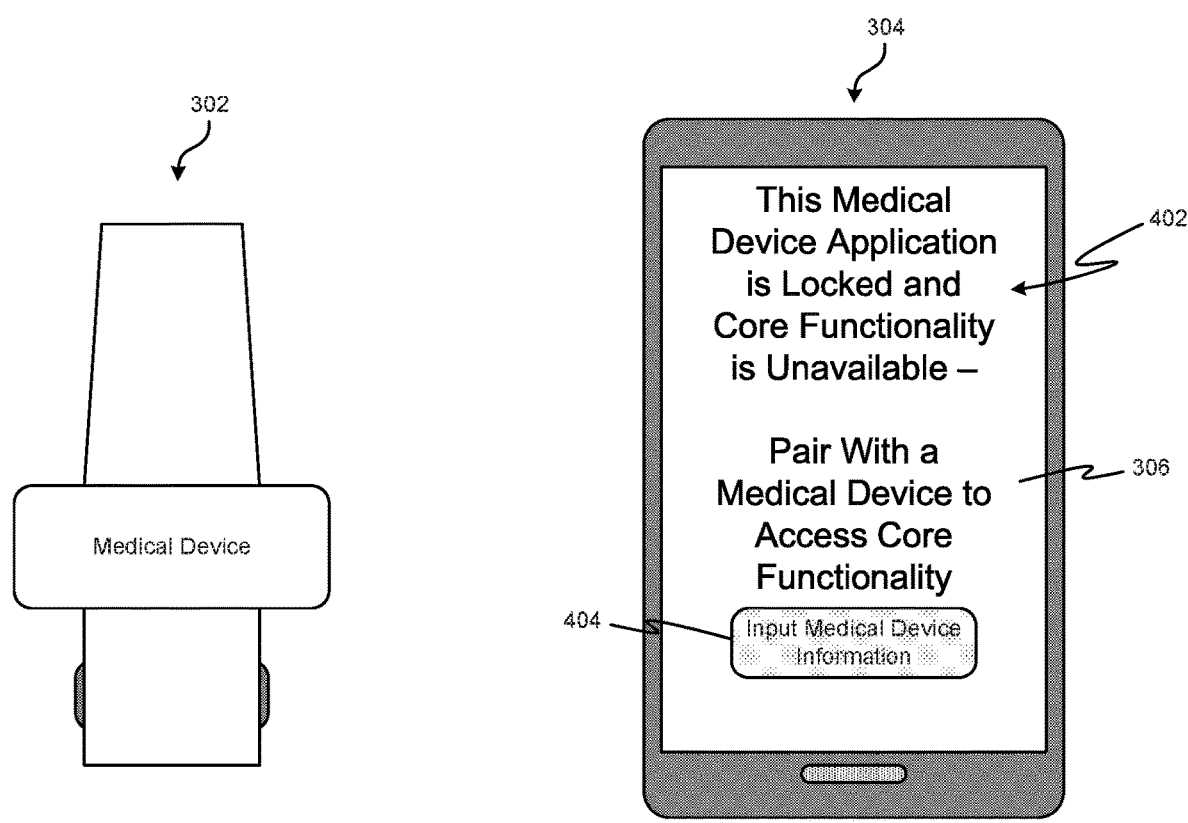
FIG. 4 shows a medical device application in a locked state, according to an embodiment of the present invention.

FIG. 4 is exemplary of an embodiment wherein a screen displays a message 402 describing that the medical device application 306 requires that the medical device 302 be paired with the medical device application 306 in order for the medical device application 306 to provide some or all of the medical device application 306 functionality. As shown, link 404 provides access to a second screen (not shown) which may provide some or all functionality, for example, the ability to input user information and medical device 302 information so that once the medical device 302 is paired with the medical device application 306, the medical device application 306 is ready to provide full or complete or desired functionality consistent with and operable by the particular medical device 302.

In another embodiment, pairing the medical device 302 to the medical device application 306 may be accomplished by simply confirming, such as by touching a button on a display screen of the computing device, that a medical device recognized by the medical device application 306 and indicated on a display of the medical device application 306 is the medical device 302 in possession of the user. The indication of the medical device 302 may comprise a unique code, some programmed name recognizable by the user, a default name of the medical device, a symbol representing the medical device, or some other indication known in the art.

In some embodiments, a medical device 302 is provided which has multiple use modes, and the medical device application 306 may similarly provide multiple use modes which correspond to the particular use modes of the medical device 302. In this embodiment, the medical device 302 is configured to unlock only the functionality of the medical device application 306 which is appropriate to the desired use mode of the medical device 302. For example, the medical device 302 may be an inhaler which may be suitable to deliver different drugs, and/or different classes of drugs, and/or different dosages. In such an example, the medical device application 306 which pairs with the medical device 302 in respect of one drug or class of drug or dosage may be different from the medical device application 306 which pairs with the medical device 302 in respect of a different drug or class of drugs or dosage. Hence the pairing and locking mode of the medical device application 306 helps to supply assurance that the different drugs are used in accordance with their respective directions and posology.

By "pairing," what is meant in one embodiment is that the medical device 302 and the medical device application 306 have connected to one another, with the medical device application 306 recognizing the medical device 302, and the medical device 302 providing at least some information to the medical device application 306.

In many embodiments, some functions may still be accessible by the user while the medical device application 306 is in the locked state, such as altering settings, inputting personal information, inputting information about the medical device 302, etc., in various approaches. However, core functionality of the medical device application 306 may only be accessed while the medical device application 306 is in the unlocked state. By the term "core functionality" is meant the particular functionality that is necessary or useful to effectuate the purpose of the device. Core functionality may differ from device to device and maybe a function of device purpose. Core functionality may include functions that enable a medical device 302 to operate, functions that allow collection of data from a medical device 302, and functions that allow the medical device application to communicate to the medical device 302. For example, if the device 302 is a substance (drug or pharmaceutical) delivery device such as an inhaler, the core functionality may comprise the aerosolization and administration to the patient of the appropriate drug.

Furthermore, in one embodiment, only functionality of the medical device application 306 that is appropriate for a particular medical device 302 may become accessible in the unlocked state, such as to prevent confusion with the operation of the medical device application 306 and/or to simplify a user interface of the medical device application 306 (such as when operating more than one type of medical device, or a medical device operable with multiple drugs, with the medical device application 306). By appropriate, what is meant in one embodiment is that the functionality is consistent with and intended for the medical device 302 and/or the intended patient.

In some embodiments, a user may possess two medical devices 302 such as smart inhalers, each smart inhaler being configured to provide one or more of a different medicament, dose, formulation, or compound. For example, one smart inhaler may provide a drug for treatment of chronic obstructive pulmonary disease (COPD) while the other smart inhaler may provide a drug for the treatment of asthma. In such embodiment(s), the medical device application 306 may therefore recognize and understand the differences between the medical devices (smart inhalers) and may only provide functionality on the medical device application 306 for the particular smart inhaler that is currently paired to the medical device application 306. In this way, particular operating parameters of the different smart inhalers together with patient posology will be accounted for and provided in the medical device application 306, for example dosage amount, frequency of dosage, drug interactions, and adverse effect warnings, when a particular smart inhaler is currently paired to the medical device application 306. As a further aspect of such embodiments, the user may possess a single medical device 302 such as a smart inhaler, however the inhaler may be configured in such a way as to permit a cartridge or magazine of doses to be functionally coupled to the inhaler. In this case, the medical device application 306 may be able to configure a functional element of the inhaler comprising medical device 302 in one manner for a first drug or class of drugs or dosage contained in one cartridge, and in a second manner for a second drug or class of drugs or dosage. Of course this aspect is not limited to only two different drugs or classes of drugs or dosage, but may apply to multiples thereof.

In another example, a heart rate indicator may be displayed on the computing device 304 through the medical device application 306 when the medical device is a heart rate monitor. However, a heart rate indicator will not be displayed when the medical device 302 is incapable of detecting a user's heart rate, such as when the medical device 302 is a smart syringe, inhaler, glucose monitor, or other non-heart rate enabled device.

Figure 5A:
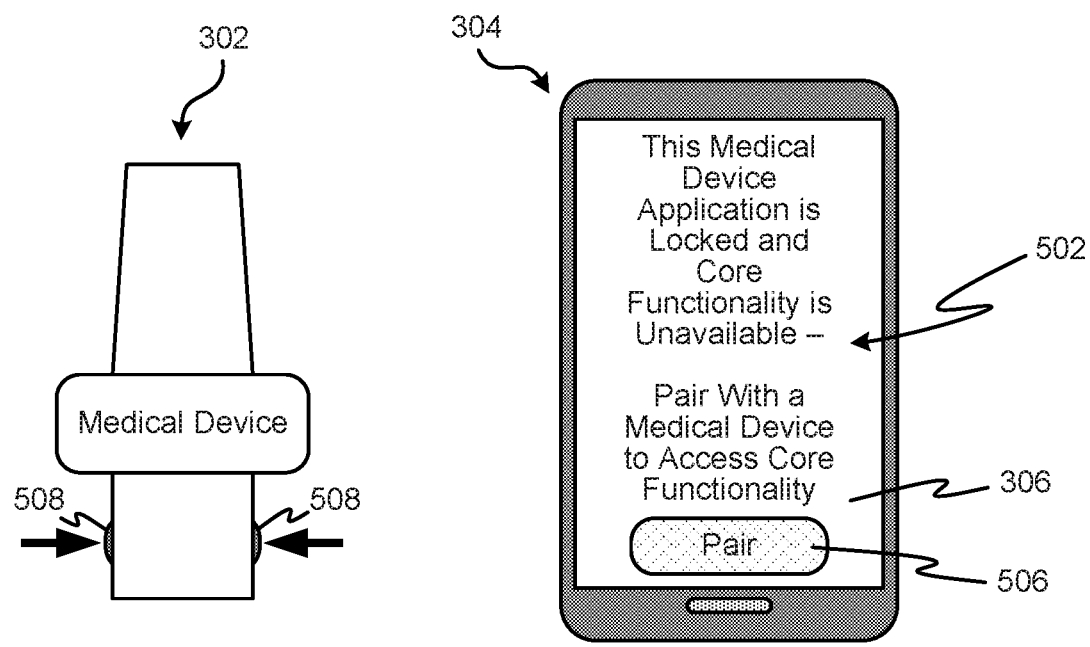
FIGS. 5A-5B show a medical device application shifting from a locked state to an unlocked state, according to an embodiment of the present invention.
Figure 5B:
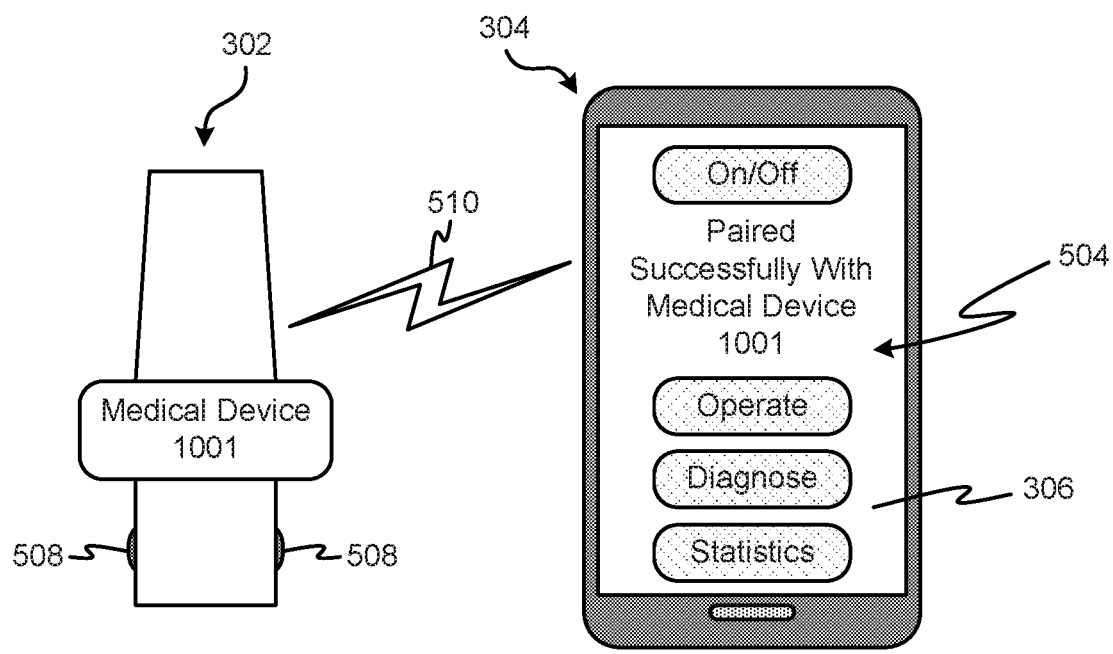

One or more of the following actions may be performed, in various embodiments, to shift the medical device application 306 from the locked state 502 to the unlocked state 504, as shown in FIGS. 5. In various embodiments, a triggering event may cause the shifting to occur, such as pushing, activating or contacting of one or more buttons 508 on the medical device 302, selection of a graphic (such as a visual representation 506 of a button, medical device) on the medical device application 306 (possibly after one or more other factors are verified, such as the identity of the user, medical device type, or proximity of the medical device 302 to the computing device 304), an attempt to utilize the medical device 302 (such as sensing the inhalation of a user through an inhaler, insertion of a needle into an arm of the user for a smart syringe, contact of a sensor pad with skin of a user for a heart rate monitor). Successful pairing is indicated by the wireless communication line 510 (FIG. 5B).

In another embodiment, in order to unlock the medical device application 306, more than one triggering event may be required. For example, more than one medical device 302 may be in the possession of a user, and unlocking the medical device application 306 may be caused by activation of buttons on both medical devices 302 within a predetermined amount of time, such as 2 seconds, 5 seconds, 10 seconds, 30 seconds, 1 minute, etc. In one example, a first medical device 302 may be an inhaler or nebulizer, while a second medical device 302 may be a medication cartridge that is insertable into the inhaler or nebulizer. In order to unlock the medical device application 306, a user may depress a button on the inhaler or nebulizer (a first trigger), while also bringing the medication cartridge within wireless sensing range of the computing device 304 (a second trigger), the proximity of the medication cartridge being sensed by the computing device 304.

Once the medical device application 306 is unlocked in this fashion, the identity of the inhaler or nebulizer and the medication cartridge may be provided to the medical device application 306, thereby allowing for dosage information to be exchanged between the medical device application 306 and the inhaler or nebulizer, among other useful exchange of information between the two medical devices 302 and the medical device application 306 on the computing device 304. In addition, the unlocking of the medical device application 306 may in turn result in the inhaler or nebulizer being unlocked and the user being able to take a dose of the medication in the cartridge via the inhaler or nebulizer. This results in increased security, and additional functionality not available in conventional medical devices and medical device applications.

Figure 6A:
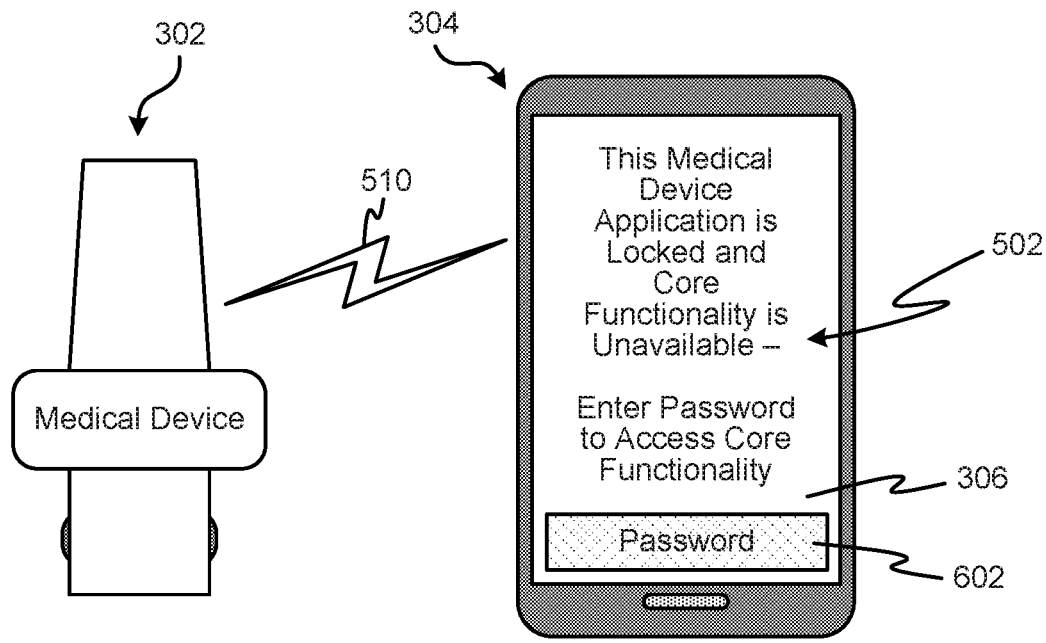
FIGS. 6A-6B show a medical device application shifting from a locked state to an unlocked state, according to an embodiment of the present invention.
Figure 6B:
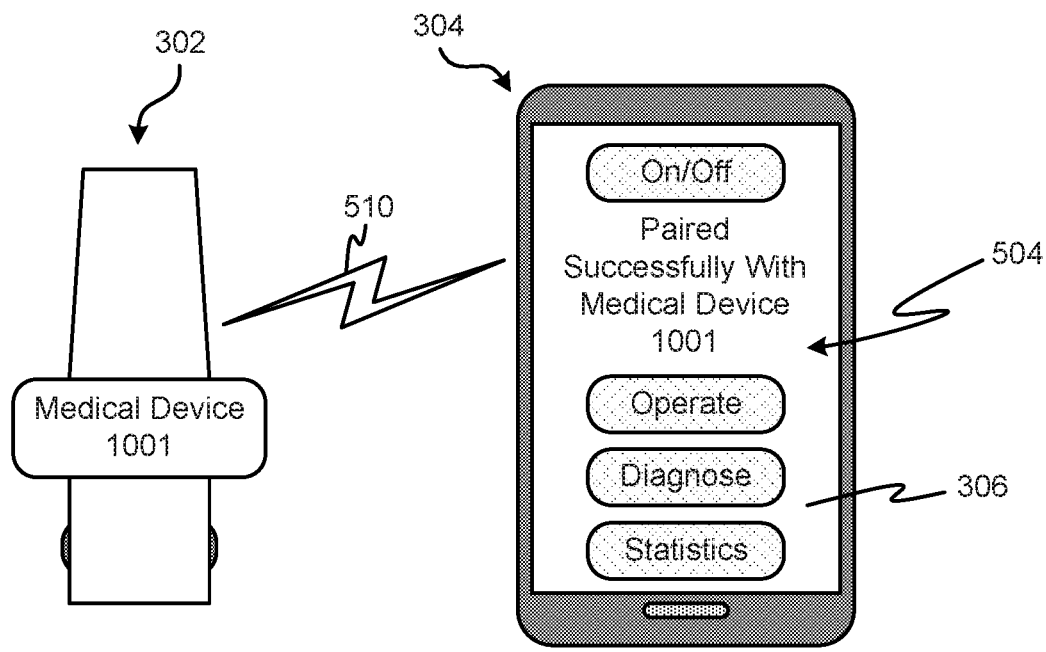

As shown in FIG. 6 in one embodiment, a password may be input into a password field 602 of the medical device application 306 while the medical device 302 is in communication with the medical device application 306 in order to shift the medical device application 306 from the locked state 502 to the unlocked state 504 (FIG. 6B). After this shift, all appropriate functionality of the medical device application 306 becomes accessible to the user, provided that the user's medical device 302 is capable of providing information to the medical device application 306, and is capable of performing actions required by the medical device application 306 to activate the appropriate functionality of the medical device application 306.

In a further embodiment, double security may be provided to the information in the medical device application 306 and to the use of the medical device 302 by requiring that not only must a password be entered in the password field 602 of the medical device application 306, but that the medical device 302 must be in use and in communication with the medical device application 306 in order to shift the medical device application 306 from the locked state 502 to the unlocked state 504.

In another embodiment, the medical device 302 may be required to be physically placed or moved to within communication range of the computing device 304 while the medical device application 306 is executing on the computing device 304 and is searching for the medical device 302, using a wireless communication technology, referred to as scanning for an available medical device. Once the medical device 302 is within communication range of the computing device 304, the medical device application 306 may automatically recognize the presence of the medical device 302, shift to the unlocked state, and allow access to all appropriate functionality for the particular medical device 302 within range of the computing device 304. By "all appropriate functionality" is meant such functionalities as are appropriate to the device, drug (if applicable) and user. This may comprise all functionalities of which the medical device application 306 is capable, or it may be a subset thereof as described herein.

In this embodiment, the medical device application 306 may still ensure that the user, for which at least some personal information has been entered into the medical device application 306, is intended to be in possession and/or capable of operating the medical device 302 which has caused the medical device application 306 to shift to the unlocked state.

In a further embodiment, should the medical device application 306 determine that the medical device 302 is not intended for use by the user, the medical device application 306 may send an alert to a server (which may be monitored by medical personnel, law enforcement, etc.), shutdown operation of the medical device 302, and/or enter a fault state where another security protocol would need to be overcome in order to access the medical device application 306 again, such as entering of a password, requesting from a provider of the medical device 302 a code and receiving the code to enter into the medical device application 306 to verify the user's identity.

According to another embodiment, a token may be wirelessly passed from the medical device 302 to the medical device application 306 in order to shift the medical device application 306 from the locked state to the unlocked state. After this shift, all appropriate functionality of the medical device application 306 may become accessible to the user, dependent upon which functionality of the medical device application 306 that the user's medical device 302 is capable of utilizing. The token may be specific and unique to at least one of: the user, the medical device 302, a medicament delivered by the medical device 302, the user/medical device combination, etc., and may be recognizable by the medical device application 306 as being indicative of the aforementioned relationship. The token may be a string of numbers, letters, characters, an alphanumeric string, or some other identifying electronic signature capable of being passed wirelessly from the medical device 302 to the medical device application 306.

In another embodiment, a predefined number of communications between the medical device 302 and the medical device application 306 during a predefined time period may be used in order to shift the medical device application 306 from the locked state to the unlocked state. After this shift, all appropriate functionality of the medical device application 306 may become accessible to the user, dependent upon which functionality of the medical device application 306 that the user's medical device 302 is capable of utilizing.

Any number of communications may be used, such as 1, 2, 3, 4, 5, 10, 20 or more, in various embodiments. Furthermore, the predefined time period may vary based on one or more factors, and may be any amount of time, for example 1 to 100 milliseconds, 1 to 10 seconds, or any value therebetween. The factors may include one or more of: a type of the medical device 302, a number of times the medical device application 306 has been accessed, a most recent access of the medical device application 306, the most recent access of the medical device 302, etc.

For example, in some embodiments, three messages sent and received within one second indicating a unique medical device indicator and a unique medical device application indicator may comprise the decision trigger to shift the medical device application 306 from the locked state to the unlocked state. An indicator may be a string of numbers, letters, characters, an alphanumeric string, or some other identifying electronic signature that is difficult to guess and long enough to be unique for all users in a certain geographic location, such as the world, a continent, a country, or other natural or political subdivision.

In some embodiments, all appropriate functionality of the medical device application 306 may be accessible after the medical device application 306 has been shifted to the unlocked state once during an initial pairing between the medical device 302 and the medical device application 306.

In other embodiments, all appropriate functionality of the medical device application 306 may be accessible as long as the medical device application 306 is maintained in the unlocked state via periodic exchange of messages between the medical device 302 and the medical device application 306 and/or according to random requests for the medical device's unique identifier.

In yet another embodiment, the medical device application 306 may be shifted to the unlocked state each time core functionality is accessed due to a user attempting to access the medical device 302, but not when non-core functionality is attempted to be accessed on the medical device application 306. In this embodiment, the use of non-core functionality on the medical device application 306 will not affect the locked/unlocked state of the medical device application 306. However, attempting to use the medical device 302 will result in the medical device application 306 shifting from the locked to the unlocked state. This embodiment is directed at cases where the medical device 302 has already been verified to be used by an appropriate user, and therefore it's pairing with the medical device application 306 is sufficient to unlock the medical device application 306.

In one embodiment, the medical device application 306 may only be operable with a single medical device 302. Therefore, during a first use of the medical device application 306, information may be provided to the medical device application 306 about the medical device 302, such as by the user, automatically upon the medical device 302 being brought within wireless communication range of the computing device 304, etc. This information about the medical device 302 may be used to ensure that no other medical device is allowed to pair to the particular instance of the medical device application 306 on the computing device 304.

In another embodiment, the medical device application 306 may be operable with more than one medical device 302. In this embodiment, during a first use of each of the medical devices 302, information may be provided to the medical device application 306 about the medical device 302, such as by the user, automatically upon the medical device 302 being brought within wireless communication range of the computing device 304.

In order for the medical device application 306 to remain in the unlocked state, the computing device 302 may monitor via one or more wireless communication channels for predefined information (transmitted from the medical device 302 and received by the computing device 304). The predefined information is captured by the medical device application 306 in an initial pairing, and then the predefined information is listened for, such as in a "heartbeat" function (i.e., a system status, periodic signal or synchronization signal) for as long as the medical device application 306 is being accessed by the user.

The heartbeat function may operate by listening for one or more communications, the one or more communications being anticipated to be received according to a predefined schedule, for example, one communication every 10 seconds. When a communication is not received, a proactive message may be sent requesting the communication to ensure that a device is still in communication with another device.

In some embodiments, the continued use of the medical device application 306 triggers a predefined series of communications between the medical device 302 and the medical device application 306 in order to ensure that the medical device 302 remains in the possession of whomever is accessing the medical device application 306, to prevent a single pairing from allowing unfettered access to the medical device application 306 by someone who is not entitled to such access, to protect the private medical information of an authorized user from unauthorized access. The messages that are sent from the medical device 302 to the medical device application 306 may be simple, for example, short packets that indicate the identity of the medical device 302 and the medical device application 306 being accessed. Furthermore, should a predetermined number of messages not be received by the medical device application 306 as anticipated (as arranged between the medical device application 306 and the medical device 302 upon the first pairing), the medical device application 306 may terminate the pairing, stop providing some or all functionality of the medical device application 306 to the user, and/or restrict access to functionality of the medical device 302.

In further embodiments, in addition to the predefined information, the medical device 302 may send payload data to the computing device 304. This payload data may include any useable information that may be gathered, sensed, tracked, created, and/or forwarded by the medical device 302, such as usage data, performance data, patient physiologic data, energy/battery level and/or battery usage, type of medicament in the medical device 302, remaining medicament level.

Some exemplary payload data that is transmitted from the medical device 302 to the medical device application 306 include total inhalation time for an inhaler, maximum flow rate during inhalation for an inhaler, minimum flow rate during inhalation for an inhaler, confirmation of device use, confirmation of medicament delivery, total delivered medicament, medicament delivery profile or rate, heart rate (for a heart rate monitor), one or more times of activation of the medical device 302, length of medical device 302 activation, among others.

The medical device application 306, upon receiving the signal from the medical device 302, may process the signal to obtain the payload data, and may then define parameters for operation of the medical device application 306. The parameters may include an image to display that matches the medical device 302, a name of the medical device to display, a type of medicament being utilized by the user and stored in the medical device 302, how to interact with the user based on the type of medical device and/or medicament being used, etc. In addition, the medical device application 306, in response to receiving the signal, may compute operating information to display to the user that is relevant to the medical device 302. Operating information may include any useful information to allow the user to utilize the medical device 302. Operating information may also comprise information which relates to patient safety, drug interactions, patient device usage data, and patient physiologic data.

In various approaches, the operating information may include one or more of the following: a number of doses of medicament to take in a certain period of time (e.g., two doses per day), times for use of the medical device 302 (e.g., check heart rate at 6:00 AM, 12:00 PM, and 6:00 PM), medicament name and drug interaction information (e.g., do not take acetaminophen with alcohol), etc.

In one embodiment, the medical device application 306 may utilize a strength of the signal received from the medical device 302 to determine a proximity of the medical device to the computing device 304. This may be useful for operation within a medical care facility, such as a hospital, nursing home, etc., to enable the computing device 304 to determine which of a plurality of signals is the "right" signal to process, e.g., the closest signal. However, the computing device 304 may cycle through the plurality of signals until the signal that provides the appropriate predefined information is located, and then may lock onto that signal to the exclusion of all others.

The medical device 302 remembers and stores computing devices to which it has been paired previously in an internal memory of the medical device, in one embodiment. The medical device, upon being unpaired, will pair to these computing devices preferentially to any other computing device(s).

Figure 7:
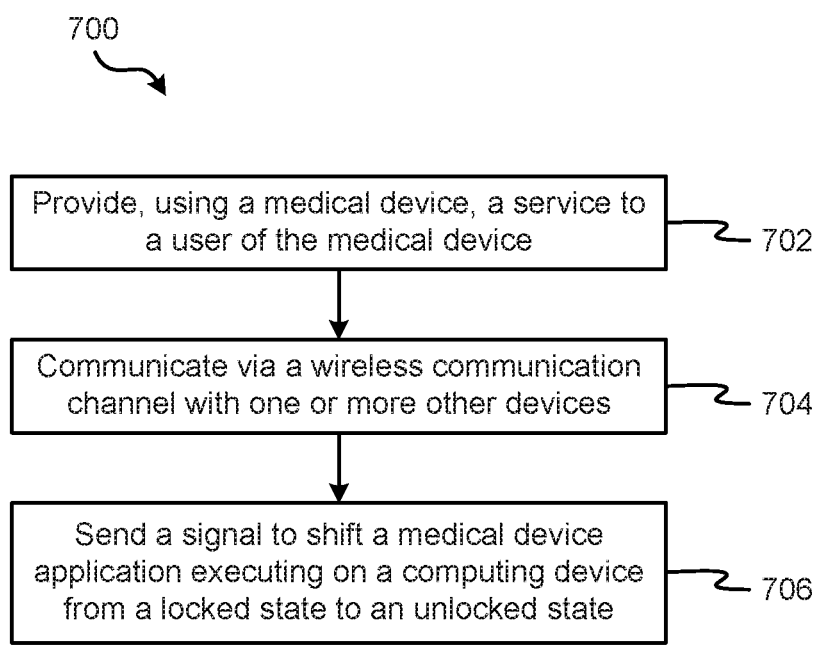
FIG. 7 shows a flowchart of a method, according to an embodiment of the present invention.

Now referring to FIG. 7, a flowchart of a method 700 is shown according to one embodiment. The method 700 may be performed in accordance with the present invention in any of the environments depicted in FIGS. 1-6, among others, in various embodiments. Of course, more or fewer operations than those specifically described in FIG. 7 may be included in method 700, as would be understood by one of skill in the art upon reading the present descriptions.

Each of the steps of the method 700 may be performed by any suitable component of the operating environment. For example, in various embodiments, the method 700 may be partially or entirely performed by a computing device, a medical device capable of communicating via one or more wireless technologies, or some other device having one or more processors therein. The processor, e.g., processing circuit(s), chip(s), and/or module(s) implemented in hardware and/or software, and preferably having at least one hardware component may be utilized in any device to perform one or more steps of the method 700. Illustrative processors include, but are not limited to, a central processing unit (CPU), an ASIC, a FPGA, CPLD, SoCs, etc., combinations thereof, or any other suitable computing device known in the art.

As shown in FIG. 7, method 700 may initiate with operation 702, where a function is provided by a medical device to a user of the medical device. Any known function, as appropriate to the medical device and intended use, may be provided. In some embodiments, the function may comprise one or more of: providing an aerosolized medicament for user inhalation, providing a liquid medicament for user injection, sensing a physiological condition of the user, sensing and ambient condition or any combination thereof.

In some exemplary embodiments, the function may comprise delivery of medicament to the lungs of the user (when the medical device is an inhaler), injection of a liquid drug into the body of the user (when the medical device is a smart syringe or insulin pump), detection of a cardiac parameter of the user (when the medical device is a cardiac sensor), delivery of a dosage form (where the medical device is a pill dispenser), and the like.

In operation 704, one or more other devices are communicated with, wirelessly via a wireless communication channel, by the medical device, such as a computing device, other medical devices, and others as described herein and/or known or developed in the art.

In operation 706, a signal is sent from the medical device to a computing device to shift a medical device application executing on the computing device from a locked state to an unlocked state. This signal may take any known form as described herein, such as one or more packets transmitted via Bluetooth, a series of transmissions made via RF, etc.

According to some optional operations, the computing device may communicate with the medical device, preferably via one or more wireless communication channels. Furthermore, the computing device may execute the medical device application using a processor of the computing device and local memory of the computing device. Also, the medical device application may be shifted from the locked state to the unlocked state in response to receiving the signal from the medical device. While the medical device application is in the locked state core functionality of the medical device application is disabled. Then, while the medical device application is in the unlocked state, at least some functionality (including at least some of the core functionality) of the medical device application that is applicable to the medical device is enabled.

According to some embodiments, the medical device may be a smart unit-dose inhaler of a type described herein, or any other known in the art, such as a multi-dose inhaler, passive inhaler, active inhaler, nebulizer, auto-injector or other dose delivery device.

In one embodiment, method 700 may further include disabling functionality of the medical device when the medical device is not in communication with the medical device application on the computing device. This operation may result in restricting access of the medical device from those who are not in possession of the medical device application and/or are not permitted to use the medical device.

In another embodiment, method 700 may further include attempting to connect with the medical device, using the computing device, in response to the user providing a trigger. The trigger may be any event, action, condition, response known in the art that is capable of being recognized by the medical device application executing on the computing device. Further, method 700 may include pairing the medical device with the medical device application on the computing device, in response to receiving this signal. Method 700 may also include sending one or more messages from the computing device to the medical device indicating parameters for operation of the medical device after pairing is successful.

In yet another embodiment, method 700 may further include sending a message from the medical device to the medical device application on the computing device in response to a triggering event. Here, the triggering event may be any action, event, condition, response known in the art that is capable of being recognized by the medical device. Further, method 700 may include pairing the medical device with the medical device application on the computing device in response to recognition of the trigger. Thereafter, method 700 may include sending one or more messages from the medical device to the medical device application indicating status and/or parameters for operation of the medical device.

In some exemplary embodiments, the triggering event may be selected from a group consisting of: the user pushing, activating or contacting a button on the medical device, the medical device being brought within a wireless communication range of the computing device, and an attempt to utilize the medical device.

In many embodiments, only functionality of the medical device application that is appropriate for a particular medical device is enabled while the medical device application is in the unlocked state, appropriate functionality being consistent with and possible when using the medical device. Therefore, functionality that is inconsistent with, impossible to use, and/or inapplicable to a certain medical device will not be enabled on the medical device application to avoid confusion, inappropriate use or misuse.

According to yet another embodiment, method 700 may further include sending a predefined series of messages from the medical device to the medical device application on the computing device after sending the signal to shift the medical device application from the locked state to the unlocked state. Method 700 may then include listening (i. e. waiting for a signal), using the medical device application on the computing device, for the predefined series of messages from the medical device. Further, method 700 may include disabling core functionality of the medical device application in response to a determination that a predetermined number of messages have not been received by the medical device application as anticipated.

In some embodiments, the medical device comprises a passive (patient inspiratory-actuated) inhaler for the delivery of medicament to the lungs of the user. One example of such an inhaler is a passive, capsule-based inhaler as described more fully in U.S. Pat. No. 8,479,730 and in U.S. Patent Publication No. 2014/0000603, the disclosures of which are fully incorporated by reference herein for all purposes.

Figure 8A:
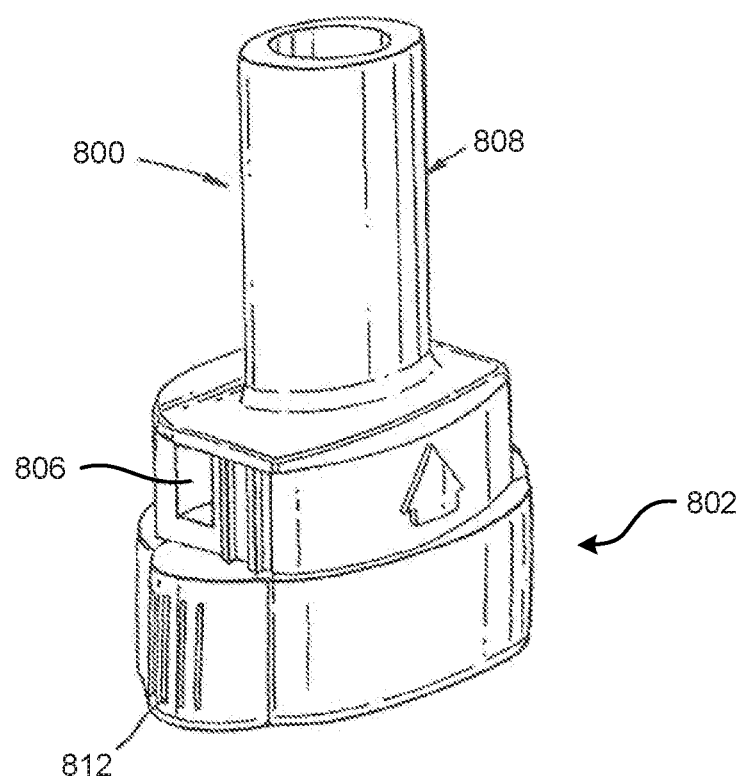
FIGS. 8A-8B are perspective views of a passive, capsule-based inhaler medical device, according to an embodiment of the present invention.
Figure 8B:
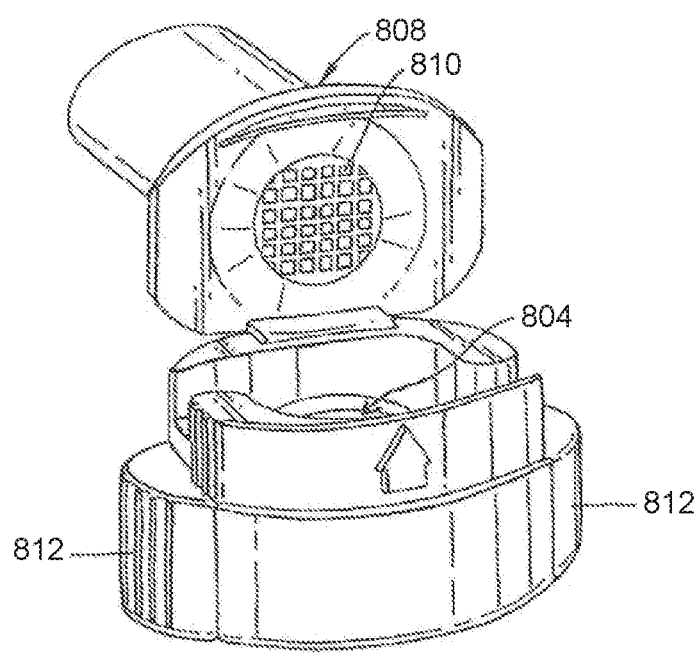

Referring to FIGS. 8A-8B, an exemplary inhaler 800 for powdered medicaments comprises, generally, a body 802 that has a recess 804 for holding a capsule (not shown) containing a powdered medicament to be inhaled, at least one air inlet 806, and a mouthpiece 808 that includes a coaxially disposed inhalation passage 810 that communicates with the recess 804 of the body 802. The body 802 has a pair of opposed biased push-buttons 812 that each include at least one piercing element (not shown) for piercing the capsule when loaded in the recess 804. The medicament is released from the pierced capsule when air is drawn through the air inlets(s) 806 into the recess 804 and swirled about therein. The mouthpiece 808 is pivotally attached to the edge of the body 802 so that it is pivotable between an open loading position and a closed dispensing position about an axis that is perpendicular to a longitudinal axis of the inhaler 800. It should be noted that the exemplary inhaler 800 is a more specific embodiment of the medical device 302 shown in FIGS. 3-6.

With continued reference to FIGS. 8A-8B, in use, the user moves the mouthpiece 808 from its closed position (FIG. 8A) to its open position (FIG. 8B) and places a capsule (not shown) containing a powdered medicament to be administered in the recess 804. The user then moves the mouthpiece back to its closed position ready for dispensing the medicament. The user presses both push-buttons 812 substantially simultaneously to activate a capsule piercing mechanism.

Once the capsule has been pierced the medicament contained therein is available to be administered by pulmonary inhalation. The user releases the push-buttons 812 and the user then grips the body 802 of the device once again. The medicament is administered by the user breathing out fully, inserting the mouthpiece 808 into the mouth, sealing the interface by placing their lips and teeth around the mouthpiece and inhaling quickly and deeply.

In some embodiments, the present invention provides an inhaler comprising a capsule housing for containing a medicament capsule, an airflow path through which air flows during an airflow event from at least one air inlet to an outlet, the airflow path passing through the capsule housing, a first sensor, a processor and a power source for powering the processor, the capsule housing being defined by at least one wall and configured such that when a capsule is located in the capsule housing and sufficient air flows along the airflow path through the capsule housing, the capsule moves within the capsule housing, the first sensor is arranged on the inhaler so that it is able to detect the movement of the capsule within the capsule housing and generate a first signal indicative of said movement, the processor receiving the first signal from the sensor and using said first signal to determine whether the first signal is indicative of the presence, or absence, of a capsule in the capsule housing during an airflow event and generate a capsule signal indicative thereof.

The inhaler is intended to enable the delivery of medicament from the capsule to an airway, for example the lung, of a user. The medicament may be a dry powder, a liquid, or some other suitable formulation and may include one or more active components for treating one or more disease states or conditions. The medicament may include one or more non-active components which may be for stabilising, bulking, and/or otherwise changing one or more characteristics of the formulation. The medicament may also be free of any active component, for example the medicament may be a placebo.

The capsule for use in the inhaler device may include a powdered medicament that is suitable for inhalation, in one embodiment. The medicament may preferably be suitable for the treatment of asthma and/or COPD, for example one or more bronchodilators, anti-muscarinics, anti-inflammatories, or combinations thereof. Preferred bronchodilators include beta-2 adrenoceptor agonists such as indacaterol, albuterol (salbutamol), salmeterol, formoterol, and pharmaceutically acceptable salts thereof.

Suitable antimuscarinic agents include ipratropium bromide, oxitropium bromide, tiotropium, glycopyrrolate, and pharmaceutically acceptable salts thereof. Suitable anti-inflammatory drugs include steroids, in particular glucocorticosteroids such as budesonide, beclomethasone dipropionate, fluticasone propionate, ciclesonide or mometasone furoate, or steroids. Other suitable actives, salts, and compounds are described in WO 00/75114, WO 04/16601, and WO 02/00679, each of which is incorporated fully herein by reference.

The sensor may be any suitable type of sensor able to generate a signal capable of being processed to provide a determination of whether a capsule is present in the inhaler. For example an optical sensor could be arranged to monitor the capsule housing and a signal from said sensor could be processed to determine if the signal is indicative of capsule movement in the capsule housing.

In some embodiments the inhaler includes a first sensor which is an impact sensor and the first signal is an impact signal. The sensor is arranged on the inhaler so that it is able to detect the movement of the capsule within the capsule housing. The sensor may detect the movement directly, for example an optical sensor viewing the capsule movement. In an alternate embodiment, the sensor may detect movement indirectly by sensing a parameter that may be analysed to determine the presence or absence of a characteristic linked with movement of the capsule, for example the impact of the capsule with a wall, or a variation in the air flow pattern as the capsule moves across air inlets or outlets.

In some more embodiments of the invention, and referring to exemplary inhaler 800 of FIGS. 8A-8B, one or both push buttons 812 (which are more specific functional embodiments of the button(s) 508 of FIG. 5) may be employed to actuate the unlock signal which is sent to the computing device to unlock the medical device application. Upon receiving the unlock signal from the inhaler, core functionality of the medical device application may be unlocked and accessible by the user.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
   a medical device configured to:
   provide a function to a user of the medical device;
   communicate via a wireless communication channel with one or more other devices; and
   send a signal to shift a medical device application from a locked state to an unlocked state; and
   a computing device comprising one or more wireless communication channels and a processor and logic integrated with and/or executable by the processor, the logic being configured to cause the computing device to:
   communicate with the medical device;
   execute the medical device application; and
   shift from the locked state to the unlocked state in response to receiving the signal from the medical device,
   wherein a functionality of the medical device application is disabled when the medical device application is in the locked state, and
   wherein a functionality applicable to the medical device is enabled when the medical device application is in the unlocked state.

2. The system as recited in claim 1, wherein the medical device is a unit-dose inhaler.

3. The system as recited in claim 1, wherein a functionality of the medical device is disabled when it is not in communication with the medical device application on the computing device.

4. The system as recited in claim 1, wherein the function comprises one or more of: providing an aerosolized medicament for user inhalation, providing a liquid medicament for user injection, and sensing a physiological condition of the user.

5. The system as recited in claim 1, wherein the computing device is selected from a group consisting of: a personal computer, a smart phone, a smart watch, a wearable device, a tablet computer, and a laptop computer.

6. The system as recited in claim 1, wherein the wireless communication channel of the medical device is configured to communicate with the wireless communication channel of the computing device via one or more radio frequencies.

7. The system as recited in claim 1, wherein the computing device is further configured to:
   attempt to connect with the medical device in response to the user providing a trigger;
   pair the medical device with the medical device application; and
   send one or more messages to the medical device indicating parameters for operation of the medical device.

8. The system as recited in claim 1, wherein the medical device is further configured to:
   send a message to the medical device application on the computing device in response to a triggering event;
   pair with the medical device application on the computing device; and
   send one or more messages to the medical device application indicating status and/or parameters for operation of the medical device.

9. The system as recited in claim 8, wherein the triggering event is selected from a group consisting of: the user depressing a button on the medical device, the medical device being brought within a wireless communication range of the computing device, and an attempt to utilize the medical device.

10. The system as recited in claim 1, wherein only functionality of the medical device application that is appropriate for a particular medical device is enabled while the medical device application is in the unlocked state, appropriate functionality being consistent with and possible when using the medical device.

11. The system as recited in claim 1, wherein the medical device is further configured to send a predefined series of messages to the medical device application on the computing device after sending the signal to shift the medical device application from the locked state to the unlocked state, and wherein the medical device application is further configured to:
   listen for the predefined series of messages from the medical device; and
   disable a core functionality of the medical device application in response to a determination that a predetermined number of messages have not been received by the medical device application as anticipated.

12. A method, comprising:
   providing, using a medical device, a function to a user of the medical device;
   communicating via a wireless communication channel with a computing device, the computing device executing a medical device application;
   sending a signal from the medical device to the computing device; and
   shifting the medical device application from a first state to a second state in response to the signal from the medical device.

13. The method as recited in claim 12,
   wherein a functionality of the medical device application is disabled when the medical device application is in the first state, and
   wherein a functionality applicable to the medical device is enabled when the medical device application is in the second state.

14. The method as recited in claim 12, wherein the medical device is a unit-dose inhaler.

15. The method as recited in claim 12, further comprising disabling functionality of the medical device when the medical device is not in communication with the medical device application on the computing device.

16. The method as recited in claim 12, wherein the function comprises one or more of: providing an aerosolized medicament for user inhalation, providing a liquid medicament for user injection, and sensing a physiological condition of the user.

17. The method as recited in claim 12, further comprising:
   attempting to connect with the medical device, using the computing device, in response to the user providing a trigger;

pairing the medical device with the medical device application on the computing device; and sending one or more messages from the computing device to the medical device indicating parameters for operation of the medical device.

18. The method as recited in claim 12, further comprising:

sending a message form the medical device to the medical device application on the computing device in response to a triggering event;

pairing the medical device with the medical device application on the computing device; and sending one or more messages from the medical device to the medical device application indicating status and/or parameters for operation of the medical device, wherein the triggering event is selected from a group consisting of: the user depressing a button on the medical device, the medical device being brought within a wireless communication range of the computing device, and an attempt to utilize the medical device.

19. The method as recited in claim 12, wherein only functionality of the medical device application that is appropriate for a particular medical device is enabled while the medical device application is in the unlocked state, appropriate functionality being consistent with and possible when using the medical device.

20. The method as recited in claim 12, further comprising:

sending a predefined series of messages from the medical device to the medical device application on the computing device after sending the signal to shift the medical device application from the first state to the second state;

listening, using the medical device application on the computing device, for the predefined series of messages from the medical device; and disabling a core functionality of the medical device application in response to a determination that a predetermined number of messages have not been received by the medical device application.

* * * * *